(12) United States Patent
Martínez-Alzamora et al.

(10) Patent No.: US 10,016,428 B2
(45) Date of Patent: Jul. 10, 2018

(54) PHARMACEUTICAL COMPOSITION OF SILDENAFIL CITRATE IN THE FORM OF A SUSPENSION FOR ORAL USE

(71) Applicants: Farmalider, S.A., Alcobendas (Madrid) (ES); Innovazone Labs LLC, Sunrise, FL (US)

(72) Inventors: Fernando Martínez-Alzamora, Alcobendas (ES); Antonia Gómez Calvo, Alcobendas (ES); Miguel Rizo Martínez, Alcobendas (ES); Nuria Sanz Menéndez, Alcobendas (ES)

( * ) Notice: Subject to any disclaimer, the term of this patent is extended or adjusted under 35 U.S.C. 154(b) by 0 days.

(21) Appl. No.: 15/076,858

(22) Filed: Mar. 22, 2016

(65) Prior Publication Data
US 2016/0279133 A1  Sep. 29, 2016

(30) Foreign Application Priority Data

Mar. 24, 2015 (ES) .................. 201500212

(51) Int. Cl.
| | |
|---|---|
| A61K 31/519 | (2006.01) |
| A61K 47/36 | (2006.01) |
| A61K 47/38 | (2006.01) |
| A61K 9/10 | (2006.01) |
| A61K 9/00 | (2006.01) |
| A61K 9/12 | (2006.01) |
| A61K 47/12 | (2006.01) |
| A61K 47/18 | (2017.01) |
| A61K 47/22 | (2006.01) |
| A61K 47/26 | (2006.01) |

(52) U.S. Cl.
CPC .......... *A61K 31/519* (2013.01); *A61K 9/0053* (2013.01); *A61K 9/10* (2013.01); *A61K 9/12* (2013.01); *A61K 47/12* (2013.01); *A61K 47/183* (2013.01); *A61K 47/22* (2013.01); *A61K 47/26* (2013.01); *A61K 47/36* (2013.01); *A61K 47/38* (2013.01)

(58) Field of Classification Search
CPC ....... A61K 31/519; A61K 47/36; A61K 47/38
See application file for complete search history.

(56) References Cited

U.S. PATENT DOCUMENTS

| | | | | |
|---|---|---|---|---|
| 5,759,579 A | * | 6/1998 | Singh .................. | A61K 9/0095 424/484 |
| 2007/0087981 A1 | * | 4/2007 | Chen .................... | A61K 9/0004 514/33 |
| 2010/0267787 A1 | * | 10/2010 | Harasymiw .......... | A61K 9/0053 514/381 |

* cited by examiner

*Primary Examiner* — Theodore R. West
(74) *Attorney, Agent, or Firm* — Cook Alex Ltd.

(57) ABSTRACT

The present invention refers to a pharmaceutical composition of sildenafil citrate in the form of a suspension for administration orally that comprises water as a vehicle and xanthan gum and hypromellose as suspension agents, that is highly stable and allows the efficient masking of the active ingredient's bitter taste. It also refers to a procedure for the preparation of said suspension and to a container that contains it and that is provided with a dosing device for its administration. This composition of sildenafil citrate in the form of a suspension is suitable for administration orally for the treatment of masculine sexual dysfunction.

9 Claims, No Drawings

PHARMACEUTICAL COMPOSITION OF SILDENAFIL CITRATE IN THE FORM OF A SUSPENSION FOR ORAL USE

TECHNICAL FIELD

The present invention refers to a pharmaceutical composition of sildenafil citrate in the form of a suspension for administration orally that is stable and that has good organoleptic properties.

PRIOR STATE OF THE ART

Sildenafil is a drug belonging to the group of selective inhibitors of phosphodiesterase-5 (PDE5), an enzyme that is responsible of the degradation of cyclic guanosine monophosphate (GMPc), such that the sildenafil promotes an increase in GMPc levels, which in turn promotes the relaxation of smooth muscle tissue.

The PDE5 enzyme is present, for example, in the pulmonary vasculature, such that sildenafil induces an increase in GMPc in the cells of the lungs' smooth muscle vasculature, which has a therapeutic application in patients affected by pulmonary hypertension due to its vasodilatory effect on the pulmonary vascular bed and on systemic circulation.

This enzyme is also present in the corpora cavernosa in the penis, sildenafil is, therefore, used in the treatment of erectile dysfunction, as an increase in GMPc levels causes the relaxation of the smooth muscles in the erectile tissue of these corpora cavernosa, allowing blood to flow into its interior, thereby promoting an erection.

Sildenafil administered orally has been shown to be an effective treatment and, in general, well tolerated in the treatment of male sexual dysfunction, as described in the article by Fink et al., *Sildenafil for male erectile dysfunction: a systematic review and meta-analysis*, Arch, Intern. Med., 2002, 162 1349-1360.

The use of sildenafil, specifically of sildenafil citrate, for this indication has been generally supported since 1998 by the main international regulatory agencies, such as the FDA (U.S. Food and Drug Administration) or the EMA (European Medicines Agency) and it is mostly sold as tablets.

Maximum plasma levels of sildenafil are reached approximately one hour after ingestion, it is therefore recommended that the drug be taken one hour before sexual activity.

Sildenafil citrate is relatively insoluble in water and it is characterised by its pronounced bitter taste, the commercially available pills are, therefore, sold in a coated form.

The ingestion of solid forms, such as tablets, can be inconvenient for some patients, in particular for those with difficulties in swallowing. Generally it can also be difficult for patients to have water available to take the medicine in time, as it must be taken within a specific time interval, as previously stated.

In order to avoid the inconveniences associated with the demands of having to swallow the sildenafil citrate tablets, the state of the art also describes other alternative ways of administration, easier for the patient, mainly chewable solid formulations or orodispersible, or even liquids, although the bitter taste of the active ingredient is always a serious obstacle in the preparation of this type of composition, as it is generally not possible to effectively mask it with the simple addition of sweeteners to the formulation.

The liquid compositions of sildenafil citrate described in the state of the art are usually alcoholic or hydroalcoholic solutions, given the low solubility of sildenafil in water.

Therefore, for example, the application for patent WO-A-2007/002125 describes a sildenafil citrate composition dissolved in a mixture of water and ethanol, for administration as a powder by the lingual and/or sublingual route, although the document makes no reference to the problem of bad taste.

The application for patent WO-A-2011/156405 describes a liquid composition of sildenafil citrate, which is dissolved in a mixture of propylene glycol and ethanol. It indicates that the composition can include flavour-masking agents and/or flavourings to reduce the bad taste.

It would be desirable to have liquid compositions of sildenafil citrate available that were completely aqueous, free of other organic co-solvents, for example in the form of an aqueous suspension, given the low solubility of sildenafil citrate in water.

In the state of the art up until now there has been no description of pharmaceutical forms of sildenafil citrate in an aqueous suspension, that are stable over the long term, that is, that do not form a sediment, or where this is minimal, such that the suspension can be completely homogenised again with only light agitation. This is essential for ensuring an adequate dose of the active ingredient. It is also necessary that the bitter taste of the sildenafil citrate be effectively masked.

There is, therefore, a continuing need for liquid formulations of sildenafil citrate in the form of an aqueous suspension suitable for oral administration, that is stable and that effectively masks the bitter taste of the sildenafil citrate.

PURPOSE OF THE INVENTION

The purpose of the present invention is a composition of sildenafil citrate in the form of an aqueous suspension for oral administration.

A procedure of the preparation of this composition also forms part of the purpose of the invention.

The use of this composition for the preparation of a medicine for the treatment of erectile dysfunction also forms part of the purpose of the invention.

The container provided with a dosing device that contains said composition also forms part of the purpose of the invention.

DETAILED DESCRIPTION OF THE INVENTION

The purpose of the present invention is a pharmaceutical composition in the form of an aqueous suspension for oral administration that comprises:
 a) sildenafil citrate as the active ingredient,
 b) xanthan gum, and
 c) hypromellose.

The authors of the present invention have developed a pharmaceutical composition of sildenafil citrate in the form of an aqueous suspension for oral administration that comprises the combination of xanthan gum and hypomellose as suspension agents that, surprisingly, have excellent organoleptic characteristics, with an effective masking of the sildenafil citrate's bitter taste, and that is also highly stable, both chemically and physically, as it remains largely homogenous over time, presenting little sedimentation and it is easily redispersed.

Throughout the present description the proportion of the different components in the invention's composition is expressed as a percentage (%) that always refers, unless specifically stated otherwise, to the percentage weight/volume (w/v), that is, it refers to the grams of said component or components per each 100 ml of the composition.

Composition with Sildenafil Citrate

The composition of the present invention is an aqueous suspension designed for oral administration.

As is well known to an expert in the field, suspensions are dispersed systems characterised by being a finely divided solid (dispersed phase) dispersed, or suspended, in a liquid dispersion medium (continuous phase).

In aqueous suspensions such as the present invention, the liquid dispersion medium is water.

In an especially preferred embodiment of the invention, the composition exclusively contains water as a dispersion medium, without any other organic solvent.

The composition in the form of a suspension in the present invention is highly stable, both chemically and physically, as it substantially maintains its homogeneity over time, presenting a low level of sedimentation and great easy of redispersion with only slight agitation.

Sildenafil Citrate

The pharmaceutical composition of the invention comprises sildenafil as its active ingredient, in the form of its salt by reaction with citric acid, know as sildenafil citrate.

Sildenafil is the International Non-proprietary Name (INN) for the product 5-[2-ethoxy-5-(4-methylpiperazin-1-yl-sulfonyl)phenyl]-1-methyl-3-n-propyl-1,6-dihydro-7H-pyrazolo[4,3-d]pyrimidin-7-one.

The sildenafil can be prepared, for example, as described in European patent application EP-A-0463756. While, its salt by reaction with citric acid can be prepared, as is well known by an expert in the field, through treatment of the sildenafil base with citric acid, as described, for example, in international patent application WO-A-2005/067936.

The composition of the invention comprises sildenafil citrate in the form of an aqueous suspension, at a concentration generally comprising between 1.5% and 5.0%, preferably comprising between 2.0% and 3.0%, more preferably comprising between 2.3% and 2.7% and more preferably still with a concentration of 2.5%, where said concentration is expressed as the equivalent concentration of sildenafil in the form of its free base.

The sildenafil citrate used to prepare the compositions in the form of a suspension in the present invention has a mean particle size generally comprising between 0.1-80 microns.

Xanthan Gum

Xanthan gum or xanthan is a high molecular weight polysaccharide formed by the repetition of a pentasaccharide of D-glucose, D-mannose and D-glucuronic acid and it is produced by bacteria from the genus *Xanthomonas*. Xanthan gum is a pharmaceutical excipient well known for its properties as a suspension, gelling and viscosifying agent among others.

Its properties, uses and specifications are well described in the well known manual of pharmaceutical excipients Rowe et al. *Handbook of Pharmaceutical Excipients*, 6$^{th}$ edition, Pharmaceutical Press, London, 2009 [ISBN: 978-0-85369-792-3].

Xanthan gum can be obtained commercially from a large number of companies, for example, under the name Keltrol® (CP Kelco) or Rhodopol® (Solvay).

The aqueous suspension of the present invention contains xanthan gum with a proportion generally comprising between 0.1% and 2.0%, preferably comprising between 0.15% and 1.0%, more preferably comprising between 0.2% and 0.5% and more preferably still comprising between 0.3% and 0.4%.

Hypromellose

Hypromellose, also called hydroxypropyl methylcellulose (HPMC), is a common excipient in pharmaceutical compositions, both in the solid and liquid form. In liquid compositions it has an application as a suspension, thickening and/or stabilising agent.

Hypromellose is a cellulose derivative whose hydroxyl groups are partially substituted, forming esters with 2-hydroxypropyl and methyl groups.

Hypromellose is available in different grades according to its higher or lower molecular weight and the degree of substitution and the greater or lesser degree to which it affects the viscosity of prepared liquid compositions. The different grades of hypromellose can be distinguished, for example, by assigning an indicative number for the apparent viscosity in mPa·s (or centipoises, cP) to an aqueous hypromellose solution of 2% weight/weight (w/w) at a temperature of 20° C.

The properties, grades and specifications of hypromellose are described in the previously cited, well known manual on pharmaceutical excipients by Rowe et al.

Hypromellose can be commercially obtained from a variety of companies, for example, from the company Dow Chemical, under the commercial name Methocel® in the range E, F, J and K.

Any grade of hypromellose can be used within the framework of the present invention. Preferably a hypromellose with a degree of viscosity comprising between 1-500 mPa·S, more preferably comprising between 1-100 mPa·S, more preferably still comprising between 2-50 mPa·S and more preferably still comprising between 2-20 mPa·S, where the viscosity, as described above, refers to standard conditions consisting of an aqueous hypromellose solution of 2% w/w at a temperature of 20° C.

In a particularly preferred embodiment of the present invention, the grade of hypromellose used is 15 mPa·S (15 cP).

The aqueous suspension for oral administration of the present invention contains hypromellose in a proportion generally comprising between 0.05% and 3.0%, preferably comprising between 0.2% and 2.0%, more preferably still comprising between 0.3% and 1.0% and more preferably still comprising between 0.4% and 0.6%.

Other Optional Components pH Regulating Agents

The invention's composition can contain substances to adjust the suspension's pH to the desired values, specifically acidifying or alkalizing substances or buffer agents.

The agents suitable for regulating the pH of the invention's compositions include, for example, potassium acetate, sodium acetate, acetic acid, adipic acid, boric acid, citric acid, hydrochloric acid, fumaric acid, malic acid, nitric acid, propionic acid, succinic acid, sulfuric acid, tartaric acid, potassium bicarbonate, sodium bicarbonate, ammonium carbonate, sodium carbonate, potassium citrate, sodium citrate, diethanolamine, ammonium phosphate, potassium phosphate, sodium phosphate, sodium glycolate, ammonium hydroxide, sodium hydroxide, sodium lactate or sodium propionate, among others, or their mixtures.

The pH regulating agent is added in sufficient quantity to achieve the desired pH values.

In a preferred embodiment of the invention, the composition has an acid pH, preferably comprising between 1.5 and 5.0, more preferably comprising between 2.0 and 4.0, more preferably still comprising between 2.5 and 3.5.

In order to achieve these acid pH conditions the composition preferably comprises a pharmaceutically acceptable acidifying agent such as, for example, acetic acid, adipic acid, boric acid, citric acid, hydrochloric acid, fumaric acid, malic acid, nitric acid, propionic acid, succinic acid, sulfuric acid, tartaric acid, among others, or their mixtures.

The acidifying agent is added in a quantity that is sufficient to achieve a pH preferably comprising between 1.5 and 5.0, more preferably comprising between 2.0 and 4.0, more preferably still comprising between 2.5 and 3.5.

In a preferred embodiment of the invention the acidifying agent is anhydrous citric acid that is added in a proportion preferably comprising between 0.25% and 1.5%, more preferably comprising between 0.4% and 0.75%.

Preservatives

The present invention's composition preferably contains a preservative agent to avoid the growth of microorganisms.

The preservatives suitable for pharmaceutical compositions for oral use are well known by an expert in the field and can be chosen from between, for example, benzoic acid, sodium benzoate or potassium benzoate, parabens such as methylparaben, ethylparaben, propylparaben and butylparaben, sorbic acid or potassium sorbate, among others, or their mixtures.

Preferably the preservative is chosen from between sodium benzoate, methylparaben, ethylparaben, propylparaben, or their mixtures.

The proportion of the preservative agent in the composition can vary depending on the specific preservative agent used, commonly the proportion is between 0.01% and 3.0%, such that an expert in the field will know how to adjust the optimal quantity for each specific preservative.

In a preferred embodiment, the present invention's composition comprises sodium benzoate as the preservative agent. Preferably, the sodium benzoate is added to the composition in a proportion comprising between 0.01% and 0.5%, more preferably comprising between 0.05% and 0.2%.

Sweeteners

The composition of the present invention preferably comprises a sweetening agent to aid in masking the bitter taste of the sildenafil citrate.

The sweeteners suitable to be used in the present invention include, for example, sodium or calcium saccharin, sucralose, aspartame, acesulfame potassium, sodium or potassium cyclamate, neohesperidin dihydrochalcone, thaumatin and their mixtures, among others.

The proportion of sweetener in the present invention's composition preferably comprises between 0.01% and 6.0%, more preferably comprising between 0.05% and 4.0%. The proportion is adjusted depending on the specific sweetener or sweeteners used and on their intensity of sweetening.

In a preferred embodiment of the invention, the composition comprises a mixture of sucralose and aspartame. In this embodiment, the sucralose is in a proportion preferably comprising between 0.1% and 4.0%, more preferably comprising between 0.5% and 3.0% and the aspartame is in a proportion preferably comprising between 0.05% and 1.0%, more preferably comprising between 0.1% and 0.5%.

In another preferred embodiment of the invention, the composition comprises a mixture of sucralose and acesulfame potassium. In this embodiment, the sucralose is in a proportion preferably comprising between 0.1% and 4.0%, more preferably comprising between 0.5% and 3.0% and the acesulfame potassium is in a proportion preferably comprising between 0.05% and 1.0%, more preferably comprising between 0.1% and 0.5%.

Flavourings

The composition of the invention can also contain flavouring agents to improve its taste and also contribute to the masking of the active ingredient's bitter taste, the sildenafil citrate.

Any pharmaceutically acceptable flavouring substance can be used, including those well known to an expert in the field, both natural and synthetic, for example, natural essential oils, such as mentha piperita, mentha arvensis, mentha crispa, eucalyptus, lime, lemon, clove, aniseed, sage or bay leaf, or fruit flavourings, whether natural or artificial including flavourings of strawberry, raspberry, apple, pineapple or apricot; among many others or in any of their mixtures.

If the composition comprises flavouring, this is commonly found in a proportion comprising between 0.01% and 2.0%.

Other Suspension/Gelling/Viscosifying Agents

The present invention's suspension can optionally contain, in addition to the xanthan gum and hypromellose, other excipients with a suspension effect, which can also simultaneously have an gelling and/or viscosifying effect on the composition.

For example, other suspension agents suitable to be included in the present invention's composition are alginic acid, sodium alginate, potassium alginate, carrageenan, guar gum, gellan gum, acacia gum, gum tragacanth, dextrin, pectin, gelatine, hydroxyethyl cellulose, hydroxypropyl cellulose, methylcellulose, microcrystalline cellulose, povidone, maltodextrin, pectin, pregelatinised starch, polycarbophil, carbomers, colloidal anhydrous silica, aluminium and magnesium silicate among others, or in their mixtures.

When the invention's composition contains other suspension agents, these are preferably in a proportion not exceeding 1.0%, more preferably not exceeding 0.5%, more preferably still not exceeding 0.3%, more preferably still not exceeding 0.2% and more preferably still not exceeding 0.1%

In a preferred embodiment of the invention, the composition in the form of a suspension does not comprise any other suspension agent in addition to the xanthan gum and the hypromellose.

Surfactants

Optionally, the present invention's composition in the form of a suspension can contain surfactant products that contribute to the improvement in its stability thanks to their capacity to modify surface tension, which also allows them to reduce interfacial tension between the continuous phases and the dispersion of the suspension.

The surfactants that can be employed in the present invention's compositions in the form of a suspension are preferably non-ionic surfactants.

For example, a non-ionic surfactant can be used that is typically chosen from between the sorbitan esters or ethoxylated sorbitan and fatty acids, ethoxylated fatty alcohols, ethoxylated alkyl phenols, ethoxylated fatty acids among others and their mixtures.

When a surfactant is added to the invention's composition it is present in a proportion preferably comprising between 0.1% and 4.0%, more preferably comprising between 0.5% and 2.0%.

The invention's compositions can additionally contain other excipients, for example, colouring or sequestering agents, etc.

In a preferred embodiment of the invention, the aqueous suspension of sildenafil citrate comprises:

sildenafil citrate with a concentration comprising between 1.5% and 5.0%, preferably comprising between 2.0% and 3.0%, more preferably comprising between 2.3% and 2.7% and more preferably still with a concentration of 2.5%, expressed as the equivalent concentration of sildenafil in the form of its free base;

xanthan gum in a proportion comprising between 0.1% and 2.0%, preferably comprising between 0.15% and 1.0%, more preferably comprising between 0.2% and 0.5% and more preferably still comprising between 0.3% and 0.4%;

hypromellose in a proportion comprising between 0.05% and 3.0%, preferably comprising between 0.2% and 2.0%, more preferably comprising between 0.3% and 1.0% and more preferably still comprising between 0.4% and 0.6%;

a preservative agent chosen from sodium benzoate, methylparaben, ethylparaben, propylparaben, or their mixtures, in a proportion comprising between 0.01% and 3.0%;

an acidifying agent chosen from acetic acid, adipic acid, boric acid, citric acid, hydrochloric acid, fumaric acid, malic acid, nitric acid, propionic acid, succinic acid, sulfuric acid, tartaric acid and their mixtures;

a sweetening agent chosen from sodium saccharin, calcium saccharin, sucralose, aspartame, acesulfame potassium, sodium or potassium cyclamate, neohesperidin dihydrochalcone, thaumatin and their mixtures, in a proportion comprising between 0.01% and 6.0%, preferably comprising between 0.05% and 4.0%;

optionally, a flavouring agent, preferably in a proportion comprising between 0.01% and 2.0%;

in which the composition's pH comprises between 1.5 and 5.0, preferably comprising between 2.0 and 4.0 and more preferably comprising between 2.5 and 3.5;

where the hypromellose used preferably has a degree of viscosity comprising between 1-500 mPa·S, more preferably comprising between 1-100 mPa·S, more preferably still comprising between 2-50 mPa·S and more preferably still comprising between 2-20 mPa·S, more preferably still it has a degree of viscosity of 15 mPa·S, where this viscosity refers to that of an aqueous hypromellose solution of 2% w/w at a temperature of 20° C.; and in which the percentages refer to percentage weight/volume (w/v).

Preferably the suspension only contains water as the dispersion medium, without any other organic solvent.

Preferably the suspension only contains hypromellose and xanthan gum as suspension agents.

In a particular preferred embodiment of the invention, the aqueous suspension of sildenafil citrate comprises:

sildenafil citrate with a concentration comprising between 1.5% and 5.0%, preferably comprising between 2.0% and 3.0%, more preferably comprising between 2.3% and 2.7% and more preferably still with a concentration of 2.5%, expressed as the equivalent concentration of sildenafil in the form of its free base;

xanthan gum in a proportion comprising between 0.1% and 2.0%, preferably comprising between 0.15% and 1.0%, more preferably comprising between 0.2% and 0.5% and more preferably still comprising between 0.3% and 0.4%;

hypromellose in a proportion comprising between 0.05% and 3.0%, preferably comprising between 0.2% and 2.0%, more preferably comprising between 0.3% and 1.0% and more preferably still comprising between 0.4% and 0.6%;

sodium benzoate in a proportion comprising between 0.01% and 0.5%, preferably comprising between 0.05% and 0.2%;

citric acid in a proportion comprising between 0.25% and 1.5%, preferably comprising between 0.4% and 0.75%;

sucralose in a proportion comprising between 0.1 and 4.0%, preferably comprising between 0.5% and 3.0%;

aspartame in a proportion comprising between 0.05% and 1.0%, preferably comprising between 0.1% and 0.5%;

optionally, a flavouring agent, preferably in a proportion comprising between 0.01% and 2.0%;

in which the hypromellose used preferably has a degree of viscosity comprising between 1-500 mPa·S, more preferably comprising between 1-100 mPa·S, more preferably still comprising between 2-50 mPa·S and more preferably still comprising between 2-20 mPa·S, more preferably still it has a degree of viscosity of 15 mPa·S, where this viscosity refers to that of an aqueous hypromellose solution of 2% w/w at a temperature of 20° C.; and in which the percentages refer to percentage weight/volume (w/v).

Preferably the suspension only contains water as the dispersion medium, without any other organic solvent.

Preferably the suspension only contains hypromellose and xanthan gum as suspension agents.

In another particular preferred embodiment of the invention, the aqueous suspension of sildenafil citrate comprises:

sildenafil citrate with a concentration comprising between 1.5% and 5.0%, preferably comprising between 2.0% and 3.0%, more preferably comprising between 2.3% and 2.7% and more preferably still with a concentration of 2.5%, expressed as the equivalent concentration of sildenafil in the form of its free base;

xanthan gum in a proportion comprising between 0.1% and 2.0%, preferably comprising between 0.15% and 1.0%, more preferably comprising between 0.2% and 0.5% and more preferably still comprising between 0.3% and 0.4%;

hypromellose in a proportion comprising between 0.05% and 3.0%, preferably comprising between 0.2% and 2.0%, more preferably comprising between 0.3% and 1.0% and more preferably still comprising between 0.4% and 0.6%;

sodium benzoate in a proportion comprising between 0.01% and 0.5%, preferably comprising between 0.05% and 0.2%;

citric acid in a proportion comprising between 0.25% and 1.5%, preferably comprising between 0.4% and 0.75%;

sucralose in a proportion comprising between 0.1% and 4.0%, preferably comprising between 0.5% and 3.0%;

acesulfame potassium in a proportion comprising between 0.05% and 1.0%, preferably comprising between 0.1% and 0.5%;

optionally, a flavouring agent, preferably in a proportion comprising between 0.01% and 2.0%;

in which the hypromellose used preferably has a degree of viscosity comprising between 1-500 mPa·S, more preferably comprising between 1-100 mPa·S, more preferably still comprising between 2-50 mPa·S and more preferably still comprising between 2-20 mPa·S, more preferably still it has a degree of viscosity of 15 mPa·S, where this viscosity refers to that of an aqueous hypromellose solution of 2% w/w at a temperature of 20° C.; and in which the percentages refer to percentage weight/volume (w/v).

Preferably the suspension only contains water as the dispersion medium, without any other organic solvent.

Preferably the suspension only contains hypromellose and xanthan gum as suspension agents.

Preparation Procedure

The present invention's composition in the form of a suspension for oral administration can be prepared by following the common procedures for the preparation of pharmaceutical suspensions, which are well known to experts in the field and which are described in the main pharmaceutical technology manuals.

For example, the composition can be prepared by following a procedure such as the one described below.

Part of the purpose of the invention is formed by a procedure to prepare the invention's composition of sildenafil citrate comprising the following stages:
  a) add the hypromellose and xanthan gum in one part water and agitate to form a homogenous dispersion of the suspension agents;
  b) separately, disperse the sildenafil citrate in another part of the composition's water; and
  c) add the dispersion obtained in stage b) to the dispersion obtained in stage a) and then add the rest of the water.

The water used for the suspension is typically purified water for pharmaceutical use, available commercially, commonly obtained by distillation, ion exchange or any other suitable method from potable water.

Stage a) of the process preferably uses between 15% and 40% of the total water, more preferably between 20% and 35% of the total water.

Preferably the water is previously heated, before adding the hypromellose and xanthan gum, to a temperature preferably comprising between 50° C. and 75° C.

After adding the hypromellose and xanthan gum the ingredients become homogenised by agitation, preferably for between 5 minutes and 45 minutes, to avoid the formation of agglomerations. Optionally, the other suspension/gelling/viscosifying agents can be added in this stage, where they are included, along with the hypromellose and xanthan gum.

Additionally, where a preservative agent is being used it can be added at this stage, for example, by previously dissolving it in the water.

A homogenous dispersion is therefore obtained in this way. This dispersion is left to cool, preferably while being continuously agitated, until reaching a temperature preferably comprising between 20° C. and 40° C. before being mixed with the dispersion obtained in stage b).

Stage b) of the process preferably uses between 45% and 75% of the total water, more preferably between 55% and 65% of the total water.

In stage b), before making the sildenafil citrate dispersion, any other of the optional ingredients being used can be dissolved in the water, such as, for example, pH regulators, sweetener(s), flavouring(s), surfactant(s), colorant(s) and or sequestering agent(s).

The sildenafil citrate is then added with continuous agitation until a homogenous dispersion is obtained.

In stage c) of the process, after mixing the dispersions prepared in stages a) and b), the mixture is homogenised by agitation, preferably for between 5 minutes and 45 minutes, until a homogenous suspension is obtained.

Finally the rest of the water is added, with continued agitation until the suspension is completely homogenised.

The suspension obtained is then dispensed into suitable containers.

For example, the suspension can be packaged in high-density polyethylene bottles, provided with a suitable dosing system such as, for example, a dose pump adapted to dispense a fixed volume of the suspension with each press.

Use of the Composition

The composition of sildenafil citrate in the present invention is indicated for the treatment of masculine erectile dysfunction. Its presentation in the form of an aqueous suspension facilitates easy oral administration while also allowing the dose to be adjusted to the particular requirements of each patient.

Additionally, the composition is stable over time and is particularly palatable, as stated in Examples 3 and 4.

This is why one of the present invention's purposes is the use of the invention's composition for the preparation of a medicine for the treatment of masculine erectile dysfunction.

Erectile dysfunction, also know as masculine sexual dysfunction, is understood to mean the persistent inability of a male to achieve or maintain an erection of the penis sufficient to have satisfactory sexual activity.

The invention's composition in the form of an aqueous suspension is suitable for oral administration, that is, for its gastric absorption.

Additionally, the composition can also be specifically administered to the buccal and/or sublingual mucous membranes, with the aim of achieving the absorption of the active ingredient across said mucous membranes.

The composition can even be administered in the oral cavity such that the aforementioned absorption routes are combined to a greater or lesser extent, that is, the product is partly ingested and partly absorbed across these mucous membranes.

The invention's composition is administered in the oral cavity, suitable adjusting the required dose of the active ingredient through measurement of the required volume of the suspension.

This can involve the use of any system that allows the volume of the oral suspension to be measured for the administration of a determined dose of sildenafil citrate, for example, an auxiliary receptacle could be used that is calibrated to measure the desired volume, or a dropper could even be used to count drops to give a determined volume, or a dose pump could even be used that is adapted to dispense a fixed volume of the suspension with each press.

In a preferred embodiment, the composition will be available in a container provided with a dosing device, typically a dosing pump, that is adapted for the administration of a fixed dose of the composition with each press.

Alternatively, this container could be an aerosol, such that the product is under pressure in the container through the use of a suitable propellant, typically an inert gas, as is well know to an expert in the field. This aerosol is preferably provided with a dose meter, such that each press dispenses a fixed amount of the composition.

Therefore, part of the present invention is formed by a container provided with a dosing device that contains the invention's composition.

Preferably, the dosing device is a dosing pump adapted to dispense a fixed volume of the suspension with each press.

Preferably, the quantity of active ingredient administered in each press comprises between 10 mg and 40 mg of sildenafil.

Surprisingly, the invention's composition presents excellent organoleptic characteristics thanks to the combination of xanthan gum and hypromellose, which contribute to effectively masking the bitter taste of the active ingredient. In addition, the suspension remains largely homogenous over time.

The following provides some illustrative examples of the present invention.

EXAMPLES

Example 1.—Sildenafil Citrate Composition in the Form of a Suspension

An aqueous suspension of sildenafil citrate was prepared using the components detailed in Table I.

TABLE I

| Component | Function | Quantity (% w/v) |
|---|---|---|
| Sildenafil citrate | Active ingredient | 3.51 |
| (sildenafil equivalent) | | (2.5) |
| Sodium benzoate | Preservative | 0.1 |
| Anhydrous citric acid | Acidifier | 0.50 |
| Xanthan gum | Suspension agent | 0.35 |
| Hypromellose 15 cP | Suspension agent | 0.50 |
| Sucralose (E-955) | Sweetener | 3.0 |
| Acesulfame potassium | Sweetener | 0.20 |
| Mentha piperita | Flavouring | 0.5 |
| Purified water | Vehicle | s.q. |
| TOTAL | | 100 |

Twenty five percent of the water was heated to 70° C. and sodium benzoate was dissolved in it. The xanthan gum and hypromellose were added to this solution under continuous agitation, with the agitation maintained for 20 additional minutes after incorporation was finished in order to achieve a homogenous dispersion of both suspension agents. The liquid was left to cool to approximately 35° C., with continued agitation.

The anhydrous citric acid, sucralose, acesulfame potassium and mint flavouring were dissolved in another vessel in 60% of the water, and sildenafil citrate was added to this solution, with continuous agitation, until a homogenous dispersion was achieved. This dispersion was added to the previously prepared dispersion containing the xanthan gum and hypromellose with continuous agitation, until total homogenisation, when the remaining 15% of the water was finally added, also with continuous agitation until a substantially homogenous suspension was obtained.

This gave an aqueous suspension with pH 3.2 with a whitish appearance and a characteristic mint smell, which contained 25 mg of sildenafil for each ml of suspension.

The suspension was packaged in high-density polyethylene bottles with 30 ml of suspension in each bottle. The bottles were provided with a dosing pump adapted to dispense 500 μl with each press, which equates to 12.5 mg of sildenafil per press.

Example 2.—Sildenafil Citrate Composition in the form Suspension

An aqueous suspension of sildenafil citrate was prepared using the components detailed in Table II.

TABLE II

| Component | Function | Quantity (% w/v) |
|---|---|---|
| Sildenafil citrate | Active ingredient | 3.51 |
| (sildenafil equivalent) | | (2.5) |
| Sodium benzoate | Preservative | 0.1 |
| Anhydrous citric acid | Acidifier | 0.50 |
| Xanthan gum | Suspension agent | 0.25 |
| Hypromellose 15 cP | Suspension agent | 0.60 |
| Sucralose (E-955) | Sweetener | 3.0 |
| Aspartame | Sweetener | 0.20 |
| Strawberry flavouring | Flavouring | 0.5 |
| Purified water | Vehicle | s.q. |
| TOTAL | | 100 |

A procedure very similar to that used in Example 1 was followed to prepare the composition, substituting aspartame for the acesulfame potassium and strawberry flavouring for the mentha piperita.

This gave an aqueous suspension with pH 3.2 with a whitish appearance and a characteristic strawberry smell, which contained 25 mg of sildenafil for each ml of suspension.

The suspension was packaged in high-density polyethylene bottles with 30 ml of suspension in each bottle. The bottles were provided with a dosing pump adapted to dispense 500 μl with each press, which equates to 12.5 mg of sildenafil per press.

Example 3.—Study into the Stability of the Invention's Composition

The stability of the product prepared in Example 1 was studied over a period of 6 months under the following conditions of temperature and humidity:
  temperature of 25° C.±2° C. and relative humidity of 65%±5%;
  temperature of 30° C.±2° C. and relative humidity of 65%±5%;
  temperature of 30° C.±2° C. and relative humidity of 75%±5%;
  temperature of 40° C.±2° C. and relative humidity of 75%±5%;

Under all the tested conditions it was observed that both the sildenafil citrate and the preservative agent remained stable, with impurity levels in all the cases of less than 0.1%, that is, less than the reporting threshold.

It was also noted that the suspension remained physically stable, with only a slight sedimentation observable, with the product becoming completely homogenised again following gentle agitation.

It can therefore be concluded that the invention's composition has good stability, both chemical and physical.

Example 4.—Comparative Organoleptic Study

A comparative study was carried out with 10 volunteers in order to evaluate the organoleptic properties of the sildenafil citrate composition in the form of an oral suspension according to the present invention.
This involved the administration of the following products to the volunteers, with the products prepared following a $2^2$ factorial design:
  i. The invention's composition prepared in Example I;
  ii. A variation of the composition prepared in Example I, retaining the hypromellose but without the xanthan gum (Comparative Example A);
  ii. A variation of the composition prepared in Example I, retaining the xanthan gum but without the hypromellose (Comparative Example B);

iv. A variation of the composition prepared in Example I, without the xanthan gum or the hypromellose (Comparative Example C).

The volunteers were asked to give an evaluation of the composition from an organoleptic point of view. The matrix of tests and results in presented in Table III:

TABLE III

| Example | Xanthan gum | Hypromellose | Evaluation |
| --- | --- | --- | --- |
| Example 1 | Yes | Yes | No bitter taste was noticed, the taste was described as agreeable |
| Comparative Example A | No | Yes | A bitter taste was noticed, the taste was described as tolerable |
| Comparative Example B | Yes | No | A bitter taste was noticed, the taste was described as tolerable |
| Comparative Example C | No | No | A very bitter taste was noticed, the taste was described as unacceptable |

It was found that only the invention's composition achieved a totally acceptable organoleptic evaluation by the volunteers, with a total masking of the bitter taste of the sildenafil citrate.

Surprisingly, it was found that when the formulated did not include one of the suspension agents, either the xanthan gum or the hypromellose, the masking of the bitter taste was clearly deficient, with the volunteers' evaluation not being positive.

The invention claimed is:

1. A pharmaceutical composition in the form of an aqueous suspension for oral administration consisting essentially of:
   a) sildenafil citrate as the active ingredient in a concentration comprised of between 1.5% and 5.0%, expressed as equivalent concentration of sildenafil free base,
   b) xanthan gum in a concentration comprised of between 0.1% and 2.0%,
   c) hypromellose in a concentration comprised of between 0.05% and 3.0%,
   d) sodium benzoate in a concentration comprised of between 0.01% and 0.5%,
   e) citric acid in a concentration comprised of between 0.25% and 1.5%,
   f) sucralose in a concentration comprised of between 0.1% and 4.0%, and
   g) acesulfame potassium in a concentration comprised of between 0.05% and 1.0%;
wherein the percentages are expressed in w/v and wherein the suspension contains water as the only dispersion medium, without any organic solvent.

2. The pharmaceutical composition according to claim 1, characterised in that the proportion of xanthan gum is comprised of between 0.2% and 0.5%, where the percentages are expressed in w/v.

3. The pharmaceutical composition according to claim 1, characterised in that the proportion of hypromellose is comprised of between 0.3% and 1.0%, where the percentages are expressed in w/v.

4. The pharmaceutical composition according to claim 1, characterised in that it comprises:
   sildenafil citrate with a concentration comprised of between 2.0% and 3.0%, expressed as the equivalent concentration of sildenafil in the form of its free base;
   xanthan gum in a proportion comprised of between 0.2% and 0.5%;
   hypromellose in a proportion comprised of between 0.3% and 1.0%;
   sodium benzoate in a proportion comprised of between 0.01% and 0.5%;
   citric acid in a proportion comprised of between 0.25% and 1.5%;
   sucralose in a proportion comprised of between 0.1% and 4.0%; and
   acesulfame potassium in a proportion comprised of between 0.05% and 1.0%;
where the percentages are expressed in w/v.

5. A pharmaceutical composition in the form of an aqueous suspension for oral administration consisting essentially of:
   a) sildenafil citrate as the active ingredient in a concentration comprised of between 1.5% and 5.0%, expressed as equivalent concentration of sildenafil free base,
   b) xanthan gum in a concentration comprised of between 0.1% and 2.0%,
   c) hypromellose in a concentration comprised of between 0.05% and 3.0%,
   d) sodium benzoate in a concentration comprised of between 0.01% and 0.5%,
   e) citric acid in a concentration comprised of between 0.25% and 1.5%,
   f) sucralose in a concentration comprised of between 0.1% and 4.0%,
   g) acesulfame potassium in a concentration comprised of between 0.05% and 1.0%, and
   h) flavoring agent;
wherein the percentages are expressed in w/v and wherein the suspension contains water as the only dispersion medium, without any organic solvent.

6. The pharmaceutical composition according to claim 5, characterized in that the proportion of flavoring agent is comprised between 0.01% and 2.0%, where the percentages are expressed in w/v.

7. A container provided with a dosing device containing a pharmaceutical composition according to claim 1.

8. A procedure for the preparation of a composition according to claim 1, comprising:
   a. adding the hypromellose and xanthan gum to one part water and agitating to form a homogenous dispersion of the suspension agents;
   b. separately, dispersing the sildenafil citrate in another part of the composition's water; and
   c. adding the dispersion obtained in stage b) to the dispersion obtained in stage a) and then adding the rest of the water,
thereby obtaining a composition according to claim 1.

9. A method for the treatment of masculine erectile dysfunction comprising administering the pharmaceutical composition of claim 1 into an oral cavity of a patient in need thereof by means of an aerosol dosing pump.

* * * * *